(12) United States Patent
Klee et al.

(10) Patent No.: US 8,853,321 B2
(45) Date of Patent: Oct. 7, 2014

(54) LASER CURABLE POLYMERISABLE COMPOSITION FOR THE PROTECTION OF HARD TISSUE

(71) Applicant: DENTSPLY International Inc., York, PA (US)

(72) Inventors: Joachim E. Klee, Radolfzell (DE); Andreas Facher, Gundetswil (CH); Chritoph Weber, Konstanz (DE); Rolf Mulhaupt, Freiburg (DE); Martin Schmider, Freiburg (DE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 14/065,682

(22) Filed: Oct. 29, 2013

(65) Prior Publication Data

US 2014/0058010 A1 Feb. 27, 2014

Related U.S. Application Data

(63) Continuation of application No. 12/215,821, filed on Jun. 30, 2008, now abandoned, which is a continuation of application No. 11/387,177, filed on Mar. 23, 2006, now abandoned.

(60) Provisional application No. 60/664,185, filed on Mar. 23, 2005.

(51) Int. Cl.
*A61K 6/08* (2006.01)
*A61K 6/087* (2006.01)
*A61K 6/00* (2006.01)

(52) U.S. Cl.
CPC .................................. *A61K 6/0017* (2013.01)
USPC ......... 524/556; 523/115; 523/118; 433/228.1

(58) Field of Classification Search
USPC ................. 524/556; 523/115, 118; 433/228.1
See application file for complete search history.

(56) References Cited

U.S. PATENT DOCUMENTS

| | | |
|---|---|---|
| 3,815,239 A | 6/1974 | Lee, Jr. et al. |
| 4,197,234 A | 4/1980 | Temin |
| 4,552,906 A | 11/1985 | Podszun et al. |
| 4,866,146 A | 9/1989 | Janda et al. |
| 5,730,601 A | 3/1998 | Bowman et al. |
| 5,908,879 A | 6/1999 | Kawashima et al. |
| 6,168,431 B1 | 1/2001 | Narusawa et al. |
| 6,325,791 B1 | 12/2001 | Shimaji |
| 2002/0120033 A1* | 8/2002 | Jia et al. .................. 523/115 |
| 2003/0104032 A1 | 6/2003 | Sawhney et al. |
| 2003/0158289 A1 | 8/2003 | Rusin et al. |
| 2004/0002036 A1 | 1/2004 | Craig et al. |
| 2004/0162375 A1 | 8/2004 | Ali et al. |
| 2006/0135643 A1 | 6/2006 | Klee et al. |

FOREIGN PATENT DOCUMENTS

| | | |
|---|---|---|
| EP | 0673637 A1 | 9/1995 |
| EP | 0678533 A2 | 10/1995 |
| EP | 0951894 A2 | 10/1999 |
| EP | 1101451 B1 | 4/2005 |
| JP | 59130806 A | 7/1984 |
| WO | 02078646 A1 | 10/2002 |
| WO | 02102909 A1 | 12/2002 |
| WO | 2004046156 A1 | 6/2004 |

* cited by examiner

*Primary Examiner* — Michael Pepitone
(74) *Attorney, Agent, or Firm* — Douglas J. Hura; David A. Zdurne; Leana Levin

(57) ABSTRACT

One-component heat-curable sealant composition for the protection of exposed dental surfaces, comprising
(a) a polymerizable monomer and/or oligomer which has at least two polymerizable double bonds per molecule, and
(b) an initiator system comprising benzoylperoxide in an amount of at least 2 wt.-% based on the total composition.

1 Claim, No Drawings

LASER CURABLE POLYMERISABLE COMPOSITION FOR THE PROTECTION OF HARD TISSUE

CROSS-REFERENCE TO RELATED APPLICATIONS

This application is a continuation application of U.S. patent application Ser. No. 12/215,821 (now abandoned) filed on Jun. 30, 2008, which is a continuation of U.S. patent application Ser. No. 11/387,177 (now abandoned) filed on Mar. 23, 2006, which is a non-provisional patent application claiming priority to U.S. Prov. Pat. App. No. 60/664,185 filed on Mar. 23, 2005, which claims priority to WO2005EP08268 filed on Jul. 29, 2005 and EP Pat. App. No. 20040018112 filed on Jul. 30, 2004.

FIELD OF THE INVENTION

The present invention relates to a one-component heat-curable sealant composition typically having a viscosity of at most 5 Pas (23° C.) for the protection of hard tissue, in particular exposed dental surfaces. The present invention also relates to a process for the protection of hard tissue, in particular exposed dental surfaces. The sealant composition is capable of undergoing a rapid rate of cure by a laser without heat-damaging neighboring tissue. The sealant composition of the invention has improved biocompatibility, high hardness, low long-term abrasion and high acid resistance.

TECHNICAL BACKGROUND

WO02/078646 discloses a dental composition containing benzoyl peroxide and for use as a root canal sealant.

Protective dental treatment for avoiding mechanical, bacterial or chemical trauma, in particular primary and secondary caries, is of increasing importance in the dental field. Pit and fissure sealants are known as compositions used in protective treatments of occlusal surfaces. Sealant materials for protective treatment of cervical surfaces exposed by gingival retraction caused by long-standing periodontitis are also known. However, such materials are characterized by high abrasion and require frequent replacements.

Dental materials can be divided into chemically (thermally) curable materials and materials polymerizing by exposure to light. Thermal polymerization is usually severely limited for applications on living tissue or other heat sensitive surfaces. Highly reactive initiators and the presence of amine accelerators are usually required whereby the shelf-life of a one-component composition is deteriorated or multi-component systems are required.

Pit and fissure sealants are typically based on methacrylate monomers. Self-curing compositions are typically two-component systems including in a first component one or more methacrylate monomers and at least one component of a free radical liberating (redox) polymerization system for said monomer(s). The monomer composition may include the peroxy type catalyst (oxidant) which is later contacted with a second component including the reducing agent (reductant) shortly prior to dental use. In case of a sealant composition, the viscosity of the composition must be low enough to allow thorough penetration of fissures and intricate interdental spaces with no air bubbles prior to polymerisation. The handling of a two-component system for providing a low-viscosity composition is highly problematic.

Light-curing compositions contain methacrylate monomers and an initiator system in a single pack. However, the storage stability of such compositions depends on the absence of light and the careful handling of the composition prior to polymerisation.

A primary object of the invention is to provide polymerizable dental sealant compositions wherein the foregoing and related disadvantages are eliminated or at least mitigated to a substantial extent.

Another object of the invention is to provide polymerizable dental sealant compositions capable of undergoing a rapid rate of cure to produce a polymerizate having strong adhesion to dentin or enamel and having excellent protective properties as a pit or fissure sealant or a sealant for exposed cervical surfaces.

Yet another object of the invention is to provide such a sealant composition having good structural stability within the environment of the human oral cavity. Still another object of the invention is to provide such a composition wherein any requirements for using higher catalyst concentrations to achieve effective rate and degree of cure are obviated.

Yet a still further object of the invention is to provide a process of utilizing such compositions to prepare a high quality polymerizate.

DISCLOSURE OF THE INVENTION

The present invention provides a one-component heat-curable sealant composition having a viscosity of at most 5 Pas (23° C.) for the protection of exposed dental surfaces, comprising
(a) a polymerisable monomer and/or oligomer, and
(b) an initiator system comprising benzoylperoxide.

The polymerizable monomers or oligomers in the one-component heat-curable sealant composition according to the invention are capable of free-radical polymerization and are preferably (meth)acrylate monomers or oligomers. The (meth)acrylate monomer or oligomer or is selected from materials having at least two, and preferably two to four polymerizable double bonds per molecule so that the cured sealant composition be crosslinked and thus better suited for use in the oral cavity. The most preferred monomers are those having two polymerizable double bonds per molecule. Monomers with a single polymerisable double-bond may be used in order to adjust the viscosity of the composition. (Meth)acrylate monomer materials useful herein are well known in the art. The preferred materials generally include monomers having a central portion containing an organic moiety and at least two (meth)acrylic end groups. Preferable monomers are ethyleneglycol dimethacrylate, diethyleneglycol dimethacrylate, dodecanediol dimethacrylate, trimethylolpropane tri (meth)acrylate, hydroxyethyl methacrylate, triethyleneglycol dimethacrylate, trimethylolpropane triacrylate, glycerine dimethacrylate, and methacrylic acid. Desirable characteristics for such monomers and/or oligomers include good film forming properties, low viscosity, low polymerization shrinkage, low water sorption and the ability to cure rapidly and completely in the mouth when irradiated with a laser. It is also desirable that the monomers be low in volatility and non-irritating to the tooth pulp. An example of preferred oligomers is a condensation product of methacryloyloxypropyl oxycarbonylamido propyltriethoxy silane. A mixture of two or more appropriate methacrylate monomers is within the scope of this invention. In fact, depending on the choice of monomers, mixture are often highly desirable to optimize the characteristics of the resulting dental composition.

Thus, it is preferred that the monomer or oligomer or monomer or oligomer blend have a viscosity of at most 5 Pas at 23° C.

In a preferred embodiment, the cured composition is not biodegradable based on the presence of biodegradable segments selected from the group of poly(lactide), poly(glycolide) and poly(caprolactone). If the cured composition is biodegradable based on the presence of biodegradable segments, the acid resistance of the cured composition will also be insufficient.

The initiator system comprises benzoylperoxide for initiating polymerization of the monomers and/or oligomers. Preferably, component (b) comprises benzoylperoxide as the only initiator. The one-component heat-curable sealant composition according to the invention preferably contains benzoylperoxid in an amount of from 0.01 to 5.0 wt.-%, preferably in an amount of from 0.1 to 2 wt-%. In a specific embodiment, the one-component heat-curable sealant composition according to the invention preferably contains benzoylperoxid in an amount of at least 2.0 wt.-% more preferably from 2.0 to 5.0 wt.-%, still more preferably in an amount of from 2.5 to 5 wt-% If desired, peroxide stabilizers such as ascorbic acid, maleic acid and the like may be included in small amounts.

In a further embodiment of the present invention, the one-component heat-curable sealant composition may further comprise a heat-curable step-growth polymerization system. The step-growth polymerization system utilized in the present invention may be an addition polymerization system (without separation or delivery of a leaving molecule) leading upon addition polymerization reaction to a polyadduct and/or a condensation polymerization system (with separation or delivery of a leaving molecule) leading upon condensation polymerization reaction to a polycondensate. Further, the step-growth polymerization system may comprise one, two or more different type(s) of monomer(s) and/or oligomer(s). In a step-growth polymerization system, monomers form in initial reaction steps intermediates or oligomers having a rather low molecular mass. These intermediates or oligomers form in the further course of reaction macromolecules. Thus, a step-growth polymerization system differs from a chain-growth polymerization system such as a free radical polymerization system in which monomers react only with a growing polymer chain. The step-growth polymerization system has the advantage that a coating having improved mechanical strength and durability may be provided. An advantage of another embodiment of the present invention of a step-growth polymerization system is that linear polymer chains may be provided, and hence a thermoplastic polymer may be provided. In a further embodiment of the present invention the dental sealant composition of the present invention comprises such thermoplastic prepolymers which may be used for forming a coating on an exposed dental surface, and thermal condensation or addition to the polymer occurs upon heating of the prepolymer on the exposed dental surface.

In another embodiment of the present invention, the dental sealant composition of the present invention comprises a step-growth polymerization system consisting essentially of monomer(s). Thus, the viscosity is advantageously low and allows easy application of the dental sealant application and provides a highly reliable sealing property of the composition. According to a preferred embodiment of the present invention the dental sealant composition provides the above described thermoplastic prepolymers upon application of the composition to an exposed dental surface.

Examples of the step-growth polymerization systems of the present invention comprise epoxide-amine, epoxide-thiol, epoxide-carboxylic acid, epoxide-carboxylic acid anhydride, epoxide-phenol, isocyanate-amine, isocyanate-alcohol, isocyanate-thiol, isothiocyanate-amine, isothiocyanate-alcohol, isothiocyanate-thiol, carboxylic acid derivative-amine, carboxylic acid derivative-alcohol, carboxylic acid derivative-thiol, acrylate-amine, acrylate-thiol, acrylamide-amine, acrylamide-thiol, maleinimide-amine, acrylate-malonic acid derivative, acrylamide-malonic acid derivative, blocked isocyanate-amine, blocked isocyanate-alcohol, SiH-En addition, and siloxane systems.

An epoxide-amine system may comprise a monomer/oligomer having at least one epoxide and one amine functionality, or it may comprise at least two different monomers/oligomers of which one monomer/oligomer comprises at least two epoxide moieties and the other monomer/oligomer comprises at least two amine groups. An epoxide-thiol system may comprise a monomer/oligomer having at least one epoxide and one thiol functionality, or it may comprise at least two different monomers/oligomers of which one monomer/oligomer comprises at least two epoxide moieties and the other monomer/oligomer comprises at least two thiol groups. An epoxide-carboxylic acid system may comprise a monomer/oligomer having at least one epoxide and one carboxylic acid functionality, or it may comprise at least two different monomers/oligomers of which one monomer/oligomer comprises at least two epoxide moieties and the other monomer/oligomer comprises at least two carboxylic acid groups. An epoxide-carboxylic acid anhydride system may comprise a monomer/oligomer having at least one epoxide and one carboxylic acid anhydride functionality, or it may comprise at least two different monomers/oligomers of which one monomer/oligomer comprises at least two epoxide moieties and the other monomer/oligomer comprises at least two carboxylic acid anhydride moieties. An epoxide-phenol system may comprise a monomer/oligomer having at least one epoxide and one phenol moiety, or it may comprise at least two different monomers/oligomers of which one monomer/oligomer comprises at least two epoxide moieties and the other monomer/oligomer comprises at least two phenol moieties.

An isocyanate-amine system may comprise at least two different monomers/oligomers of which one monomer/oligomer comprises at least two isocyanate moieties and the other monomer/oligomer comprises at least two amine groups. An isocyanate-alcohol system may comprise a monomer/oligomer having at least one isocyanate and one alcohol functionality, or it may comprise at least two different monomers/oligomers of which one monomer/oligomer comprises at least two isocyanate moieties and the other monomer/oligomer comprises at least two alcohol groups. An isocyanate-thiol system may comprise a monomer/oligomer having at least one isocyanate and one thiol functionality, or it may comprise at least two different monomers/oligomers of which one monomer/oligomer comprises at least two isocyanate moieties and the other monomer/oligomer comprises at least two thiol groups.

An isothiocyanate-amine system may comprise at least two different monomers/oligomers of which one monomer/oligomer comprises at least two isothiocyanate moieties and the other monomer/oligomer comprises at least two amine groups. An isothiocyanate-alcohol system may comprise a monomer/oligomer having at least one isothiocyanate and one alcohol functionality, or it may comprise at least two different monomers/oligomers of which one monomer/oligomer comprises at least two isothiocyanate moieties and the other monomer/oligomer comprises at least two alcohol groups. An isothiocyanate-thiol system may comprise a monomer/oligomer having at least one isothiocyanate and one thiol functionality, or it may comprise at least two different monomers/oligomers of which one monomer/oligomer comprises at least two isothiocyanate moieties and the other monomer/oligomer comprises at least two thiol groups.

A carboxylic acid derivative-amine system may comprise a monomer/oligomer having at least one carboxylic acid derivative and one amine functionality, or it may comprise at least two different monomers/oligomers of which one monomer/oligomer comprises at least two carboxylic acid derivative moieties and the other monomer/oligomer comprises at least two amine groups. A carboxylic acid derivative-alcohol system may comprise a monomer/oligomer having at least one carboxylic acid derivative and one alcohol functionality, or it may comprise at least two different monomers/oligomers of which one monomer/oligomer comprises at least two carboxylic acid derivative moieties and the other monomer/oligomer comprises at least two alcohol groups. A carboxylic acid derivative-thiol system may comprise a monomer/oligomer having at least one carboxylic acid derivative and one thiol functionality, or it may comprise at least two different monomers/oligomers of which one monomer/oligomer comprises at least two carboxylic acid derivative moieties and the other monomer/oligomer comprises at least two thiol groups. The carboxylic acid derivative may be an carboxylic acid, a carboxylic acid anhydride, a carboxylic acid ester or a carboxylic acid halide or nitrile. The halide in the carboxylic acid halide is preferably a bromide or chloride. In case of a carboxylic acid halide, the dental sealant composition of the present invention comprises preferably also a hydrogen halide scavenger, e.g. a tertiary amine. In case of a nitrile, it is preferred that the nitric is not harmful.

A preferred example of a carboxylic acid derivative-amine system comprises an aromatic tetracarboxylic acid dianhydride, e.g. pyromellitic dianhydride or pyrazine tetracarboxylic dianhydride, as a carboxylic acid derivative and an aliphatic or aromatic diamine, e.g. 4,4'-oxydianiline or diaminothiadiazole, as an amine. Such a system leads upon a condensation polymerization to a polyimide.

A further preferred example of a carboxylic acid derivative-amine system comprises an aromatic dicarboxylic acid halide, e.g. terephthalic acid dichloride, as a carboxylic acid derivative and an aromatic diamine, e.g. 4,4'-diamino-biphenyl-3,3'-diol (or 3,3'-dihydroxybenzidine), as an amine. Such a system leads upon a condensation polymerization to a polybenzoxazole.

An acrylate-amine system may comprise at least two different monomers/oligomers of which one monomer/oligomer comprises at least two acrylate moieties and the other monomer/oligomer comprises at least two amine groups. An acrylate-thiol system may comprise a monomer/oligomer having at least one acrylate and one thiol functionality, or it may comprise at least two different monomers/oligomers of which one monomer/oligomer comprises at least two acrylate moieties and the other monomer/oligomer comprises at least two thiol groups.

An acrylamide-amine system may comprise a monomer/oligomer having at least one acrylamide and one amine functionality, or it may comprise at least two different monomers/oligomers of which one monomer/oligomer comprises at least two acrylamide moieties and the other monomer/oligomer comprises at least two amine groups. An acrylamide-thiol system may comprise a monomer/oligomer having at least one acrylamide and one thiol functionality, or it may comprise at least two different monomers/oligomers of which one monomer/oligomer comprises at least two acrylamide moieties and the other monomer/oligomer comprises at least two thiol groups.

A maleinimide-amine system may comprise at least two different monomers/oligomers of which one monomer/oligomer comprises at least two maleinimide moieties and the other monomer/oligomer comprises at least two amine groups. A maleinimide-thiol system may comprise a monomer/oligomer having at least one maleinimide and one thiol functionality, or it may comprise at least two different monomers/oligomers of which one monomer/oligomer comprises at least two maleinimide moieties and the other monomer/oligomer comprises at least two thiol groups.

An acrylate-malonic acid derivative system may comprise a monomer/oligomer having at least one acrylate and one malonic acid derivative functionality, or it may comprise at least two different monomers/oligomers of which one monomer/oligomer comprises at least two acrylate moieties and the other monomer/oligomer comprises at least two malonic acid derivative groups. An acrylamide-malonic acid derivative system may comprise a monomer/oligomer having at least one acrylamide and one malonic acid derivative functionality, or it may comprise at least two different monomers/oligomers of which one monomer/oligomer comprises at least two acrylamide moieties and the other monomer/oligomer comprises at least two malonic acid derivative groups.

A blocked isocyanate-amine system may comprise a monomer/oligomer having at least one blocked isocyanate and one amine functionality, or it may comprise at least two different monomers/oligomers of which one monomer/oligomer comprises at least two blocked isocyanate moieties and the other monomer/oligomer comprises at least two amine groups. A blocked isocyanate-alcohol system may comprise a monomer/oligomer having at least one blocked isocyanate and one alcohol functionality, or it may comprise at least two different monomers/oligomers of which one monomer/oligomer comprises at least two blocked isocyanate moieties and the other monomer/oligomer comprises at least two alcohol groups.

A SiH-En addition system is preferably a silane-acrylate, silane-allylether, silane-vinylether, silane-acrylamide, or silane-maleinimide system. A silane-acrylate system may comprise a monomer/oligomer having at least one silane and one acrylate functionality, or it may comprise at least two different monomers/oligomers of which one monomer/oligomer comprises at least two silane moieties and the other monomer/oligomer comprises at least two acrylate groups. A silane-allylether system may comprise a monomer/oligomer having at least one silane and one allylether functionality, or it may comprise at least two different monomers/oligomers of which one monomer/oligomer may comprise at least two silane moieties and the other monomer/oligomer may comprise at least two allylether groups. A silane-vinylether system may comprise a monomer/oligomer having at least one silane and one vinyl ether functionality, or it may comprise at least two different monomers/oligomers of which one monomer/oligomer may comprise at least two silane moieties and the other monomer/oligomer may comprise at least two vinylether groups. A silane-acrylamide system may comprise a monomer/oligomer having at least one silane and one acrylamide functionality, or it may comprise at least two different monomers/oligomers of which one monomer/oligomer may comprise at least two silane moieties and the other monomer/oligomer may comprise at least two acrylamide groups. A silane-maleinimide system may comprise a monomer/oligomer having at least one silane and one maleinimide functionality, or it may comprise at least two different monomers/oligomers of which one monomer/oligomer may comprise at least two silane moieties and the other monomer/oligomer may comprise at least two maleinimide groups.

A siloxane system may comprise at least one siloxane having at least two alkoxy groups, preferably selected from methoxy, ethoxy, and propxy groups, bonded to one or more than one Si-atom; most preferred are methoxy groups.

According to a preferred embodiment of the present invention, the dental sealant composition may comprise a step-growth polymerization system which is a condensation polymerization system. Preferably, the condensation polymerization system is selected from the group consisting of carboxylic acid derivative-amine, carboxylic acid derivative-alcohol, carboxylic acid derivative-thiol, blocked isocyanate-amine, and blocked isocyanate-alcohol systems as described above.

In a particular preferred embodiment of the present invention, the dental sealant composition may comprise a blocked isocyanate system comprising a monomer and/or oligomer having a terminal moiety of the following formula:

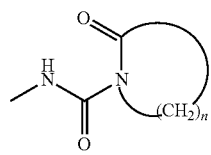

wherein n is an integer of from 3 to 15, preferably 5 to 7. The step-growth polymerization systems including a blocked isocyante have the advantage that they are suited as a one-component system. When a blocked isocyanate is reacted with an amine a urea linkage is formed. In other words a blocked isocyanate-amine system leads to a polyurea. When a blocked isocyanate is reacted with an alcohol a urethane linkage is formed. In other words a blocked isocyanate-alcohol system leads to a polyurethane. Most preferred is a blocked isocyanate system wherein n is 5. In such a system caprolactam is separated or delivered upon condensation polymerization.

The dental sealant composition of the present invention may comprise preferably at least one blocked isocyanate selected from the group of compounds having the following formulae I to IV:

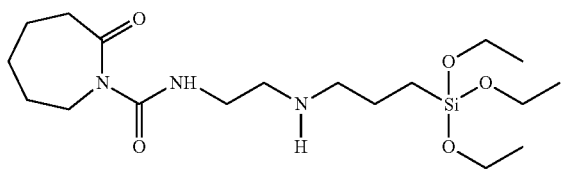

I

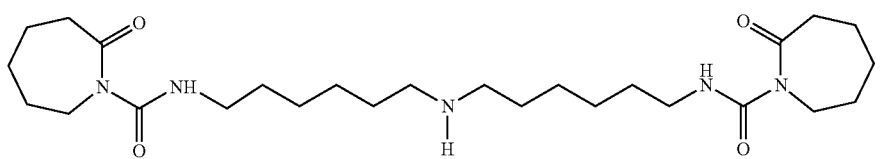

II

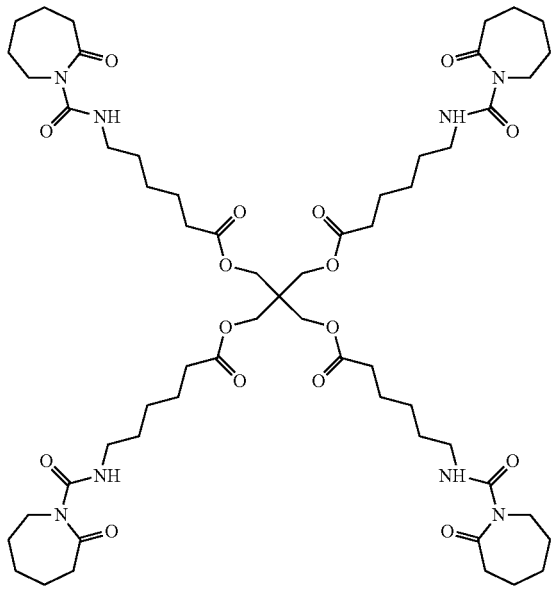

III

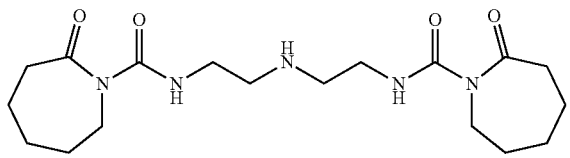

IV

Desirable characteristics of the monomer(s) and/or oligomer(s) of the step-growth polymerization system of the present invention include good film forming property, low viscosity, low polymerization shrinkage, low water sorption and the ability to cure rapidly and completely in the mouth when irradiated with a laser. It is also desirable that the monomers/oligomers are low in volatility and non-irritating to the tooth pulp. Thus, the dental sealant composition according to present invention contains the heat-curable step-growth polymerization system preferably in an amount of from 10 to 99 wt.-%.

In case that a particularly low viscosity is desired, it is preferred that the step-growth polymerization system of the present invention contains mostly monomer(s) and only a small amount of oligomer(s). In case that polymerization shrinkage should be optimized the amount of oligomer(s) may be increased.

The sealant composition according to the invention may advantageously be polymerized by locally heating the composition at a temperature of between 100 and 250° C., preferably between 160 to 220° C. without damage of hard tissue whereby a dental/medical coating is obtained. Preferably such local heating is conducted by exposure to laser light, microwave energy, or ultrasound.

The one-component heat-curable sealant composition may further comprise (d) a filler or a precursor thereof. The filler may be an inorganic filler or an organic filler or a mixture thereof. The one-component heat-curable sealant composition may contain a precursor for a filler, namely preferably one or more alkoxysilane compounds undergoing polycondensation reactions during heat curing of the composition, thereby forming the filler. The inorganic particulate filler employed in the compositions of this invention include fused silica, quartz, crystalline silica, amorphous silica, soda glass beads, glass rods, ceramic oxides, particulate silicate glass, radiopaque glasses (barium and strontium glasses), and synthetic minerals. It is also possible to employ finely divided materials and powdered hydroxyl-apatite, although materials that react with silane coupling agents are preferred. Also available as a filler are colloidal or submicron silicas coated with a polymer. Small amounts of pigments to allow matching of the composition to various shades of teeth can be included. The filler particles would be generally smaller than about 5 microns in diameter and preferably smaller than 3 μm, preferably in a range of from 3 to 500 nm. The filler in the dental sealant composition according to the invention may preferably comprise fine polytetrafluoroethylene particles. The dental sealant composition according to the invention may contain the filler or precursor thereof in an amount of from 0 to 30 wt.-%.

The dental sealant composition according to the invention has a viscosity of at most 5 Pa·s at 23° C. Such a composition has the advantage that it allows thorough penetration of fissures and intricate interdental spaces with no air bubbles prior to polymerization. Hence, in a particular preferred embodiment of the present invention, the dental sealant composition is a pit and fissure sealant or a cervical surface sealant.

In a further preferred embodiment of the present invention, the filler comprises a nanofiller, particularly modified silica according to the following formula:

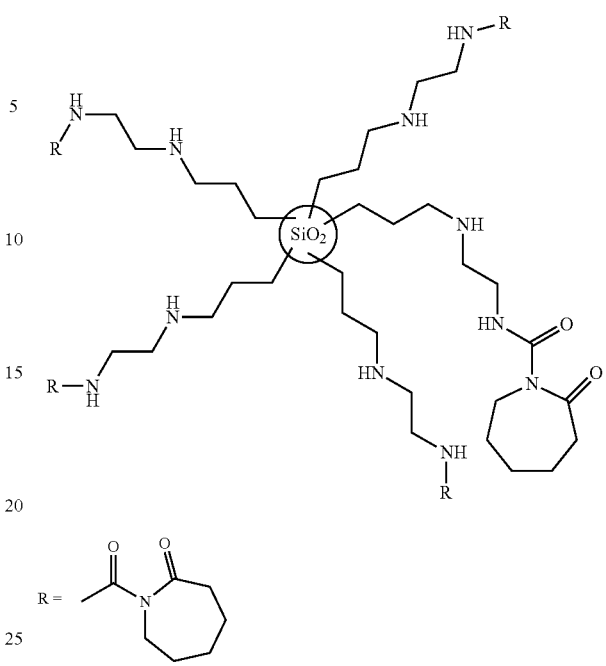

The one component heat-curable sealant composition may further comprise a solvent, preferably in an amount of from 0 to 70 wt.-%. Suitable solvents are selected from organic solvents such as acetone, ethanol, tert-butyl alcohol, ethylmethylketone, and/or chloroform.

The dental sealant composition of the present invention is a one-component system. A "one-component system" means in this specification that the chain and optionally growth-step polymerization systems of the present invention are rather shelf-stable at room temperature, such that a polymerization reaction of the monomer(s) and/or oligomer(s) of such a one-component system does essentially not occur at room temperature, but requires elevated temperatures. Therefore, the one-component system according to the present invention may comprise only one type of monomer/oligomer as a reactive ingredient having at least two functional groups of which one functional group is reactive with the other functional group. Alternatively, a one-component system according to the present invention may comprise e.g. at least two monomers/oligomers as reactive ingredients of which one monomer/oligomer comprises at least two functional groups that are reactive with at least two functional groups of the other monomer. Preferably, a one-component system of the present invention is shelf-stable at room temperature for an extended period of time, preferably for at least 3 months, more preferably at least 6 months, most preferably for a period of at least 12 months, without substantial polymerization reaction of the ingredient(s) of the one-component system. Such a one-component system has the advantage that mixing prior to use is not necessary. Thus, accuracy and reliably curing is improved and mixing errors are avoided. Moreover, a time consuming mixing step and equipment for mixing during a chair-side application is eliminated. Preferably, such a one-component system comprises a heat-curable step-growth polymerization system that is selected from the group consisting of epoxidearylamine, epoxide-cycloalkylamine, isocyanate-alcohol, blocked isocyanate-amine, and blocked isocyanate-alcohol systems.

The present invention further provides a process for the protection of exposed dental surfaces or heat sensitive dental products, which comprises the following steps:

(a) applying the one-component heat-curable sealant composition having a viscosity of at most 5 Pas (23° C.) of the invention to an exposed surface of a tooth for providing a coating on the exposed surface of the tooth, and (b) heating the coating obtained in step (a) to a temperature of at least 100° C. for curing the coating and forming a protective sealant coating.

Heating may be performed by exposure to laser light, microwave energy, infrared light or ultrasound, whereby exposure to laser light is preferred. The process of the present invention has the advantage that the temperature inside a tooth to which the dental sealant composition of the present invention is applied is increased only by 5 Kelvin units (5° C.), although the outside of the tooth may heated up to 250° C., preferably up to 180° C., upon heating. Thus, no uncomfortable heat is recognized by a patient, e.g. during a chair side application, since e.g. the temperature of the pulp of a tooth is increased only by up to 5 Kelvin (5° C.). Furthermore, no danger of destruction arises in case of an application of the dental sealant composition of the present invention to an artificial tooth having heat sensitive portions inside or in case of application of the dental sealant composition of the present invention to another heat sensitive dental product. According to a preferred embodiment of the invention heating is conducted by applying a laser. Thus, the intensity of irradiation and the amount of applied energy may be easily adjusted, preferably by adjusting the pulses of the laser.

In preferred embodiments of the present invention, the protective sealant coating is formed on pits or fissures of a tooth or on a cervical surface of a tooth by the process according to the invention. Therefore, the one-component heat-curable sealant composition according to the invention preferably is a pit and fissure sealant or a cervical surface sealant.

The present invention further relates to a kit-of-parts comprising a dental sealant composition according to the invention and a laser. The present invention further relates to the use of a dental sealant composition according to the invention for the protection of a tooth.

The following examples and comparative examples are illustrative of embodiments of the invention. All parts and percentages are by weight. Dynamic viscosities may be measured by using a Bohlin CS50 rheometer at 23° C.

EXAMPLE 1

5.820 g resin matrix composed of dodecanediol dimethacrylate and a condensation product of methacryloyloxypropyl oxycarbonylamido propyltriethoxy silane, 3.880 tetraethoxy silane, 0.300 g dibenzoyl peroxide were homogeneously mixed for obtaining a mixture.

In order to dry a dentin surface, laser light was applied in a pulse sequence of 10×4 pulses ($F_{up}$=0.5 J/cm$^2$; $f_{up}$=100 Hz; f=1 Hz). Subsequently, approximately 10 μl of the mixture prepared above were applied homogeneously on dentin that was previously etched for 45 s by using of 37% age $H_3PO_4$. Then this layer was irradiated by the following pulses: 5×, 10×4 pulses ($F_{up}$=0.9 J/cm$^2$; $f_{up}$=100 Hz; f=1 Hz) and 1× and 5×4 pulses ($F_{up}$=1.2 J/cm$^2$; $f_{up}$=100 Hz; f=1 Hz).

The formed layer had a thickness of approximately 7 μm. It withstand a wipe test and scratch test. Furthermore, the material was thermocycled for 2400 cycles at 4 and 65° C. After that treatment the material layer withstands a tooth-brush abrasion test.

COMPARATIVE EXAMPLE 1

In order to dry dentin surface the Laser was applied in a pulse sequence of 10×4 pulses ($F_{up}$=0.5 J/cm$^2$; $f_{up}$=100 Hz; f=1 Hz) Thereafter, Seal & Protect (Dentsply De Trey) was applied homogeneously on dentin that prior was etch for 45 s by using of 37% age $H_3PO_4$. Then this layer was irradiated by the following pulses: 5×, 10×4 pulses ($F_{up}$=0.9 j/cm$^2$; $f_{up}$=100 Hz; f=1 Hz) and 1× and 5×4 pulses ($F_{up}$=1.2 J/cm$^2$; $f_{up}$=100 Hz; f=1 Hz).

The formed layer has a thickness of approximately 10 μm. It do not withstand a wipe and a scratch test. Furthermore, the material was thermocycled for 2400 cycles at 4 and 65° C. After that treatment the material layer withstands not a toothbrush abrasion test and was flaking form the tooth surface.

The invention claimed is:

1. One-Component heat-curable sealant composition for the protection of exposed dental surfaces, comprising
   a) at least one blocked isocyanate selected from the group consisting of

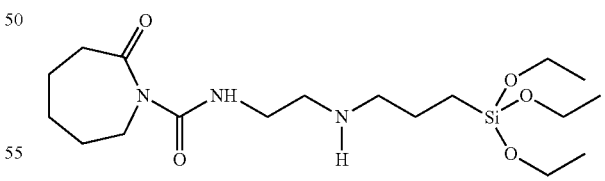

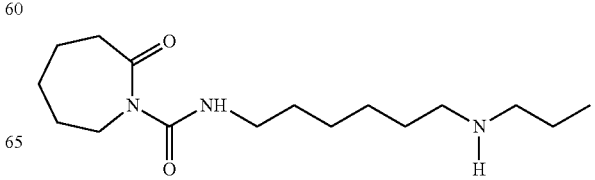

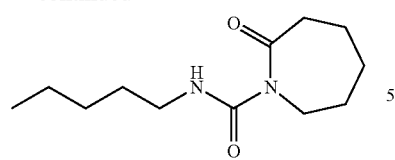
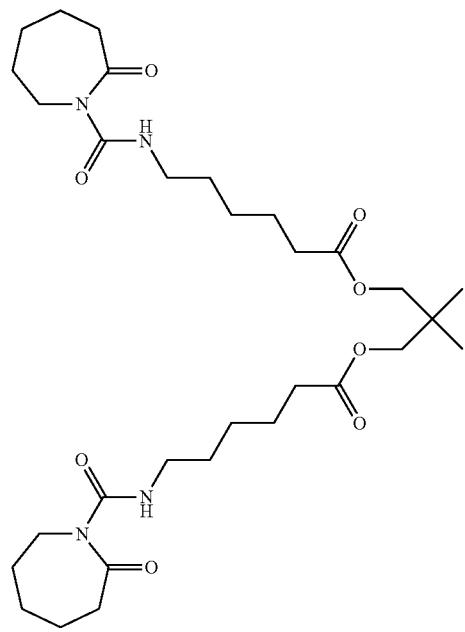
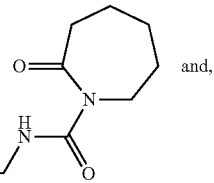
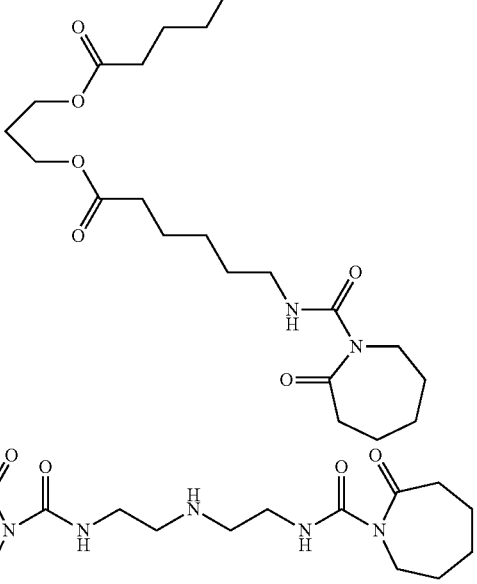
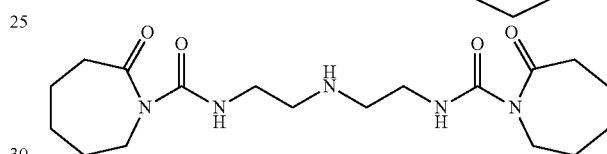
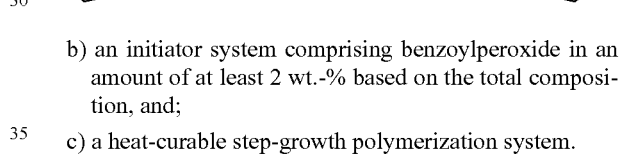
b) an initiator system comprising benzoylperoxide in an amount of at least 2 wt.-% based on the total composition, and;
c) a heat-curable step-growth polymerization system.
* * * * *